US011202595B2

(12) United States Patent
Barlow et al.

(10) Patent No.: US 11,202,595 B2
(45) Date of Patent: Dec. 21, 2021

(54) MUSCLE ASSESSMENT SYSTEM AND METHOD

(71) Applicant: NUTECH VENTURES, Lincoln, NE (US)

(72) Inventors: Steven M. Barlow, Lincoln, NE (US); Jacob L. Greenwood, Lincoln, NE (US)

(73) Assignee: NUTECH VENTURES, Lincoln, NE (US)

(*) Notice: Subject to any disclaimer, the term of this patent is extended or adjusted under 35 U.S.C. 154(b) by 342 days.

(21) Appl. No.: 16/097,252

(22) PCT Filed: Apr. 28, 2017

(86) PCT No.: PCT/US2017/030221
§ 371 (c)(1),
(2) Date: Oct. 27, 2018

(87) PCT Pub. No.: WO2017/190062
PCT Pub. Date: Nov. 2, 2017

(65) Prior Publication Data
US 2019/0110734 A1 Apr. 18, 2019

Related U.S. Application Data

(60) Provisional application No. 62/329,145, filed on Apr. 28, 2016.

(51) Int. Cl.
A61B 5/22 (2006.01)
A61B 5/11 (2006.01)
A61B 5/00 (2006.01)

(52) U.S. Cl.
CPC ........... A61B 5/228 (2013.01); A61B 5/1107 (2013.01); A61B 5/224 (2013.01); A61B 5/4519 (2013.01);
(Continued)

(58) Field of Classification Search
CPC ......... A61B 5/038; A61B 5/224; A61B 5/225; A61B 5/228; A61B 5/1107; A61B 5/45;
(Continued)

(56) References Cited

U.S. PATENT DOCUMENTS 4,501,148 A * 2/1985 Nicholas ............... A61B 5/1107
73/379.08
5,119,831 A * 6/1992 Robin .................... A61B 5/228
600/587

(Continued)

FOREIGN PATENT DOCUMENTS

KR 10-2011-0008953 A 1/2011

OTHER PUBLICATIONS

International Search Report and Written Opinion for PCT Application No. PCT/US2017/030221; dated Aug. 17, 2017; 9 pages.
(Continued)

Primary Examiner — David J. McCrosky
(74) Attorney, Agent, or Firm — Vivacqua Crane PLLC

(57) ABSTRACT

A system and method are described for assessing muscle parameters (e.g., force(s) exerted, force dynamics, strength, voluntary muscle movement, etc.) in a diagnostic or therapeutic environment. The muscle parameter assessment system includes a force-gauging device and a computing device. The force-gauging device includes at least one pressure-sensing component (e.g., transducer, pressure sensor, etc.) configured to respond to a force applied by a subject and produce one or more output signals. The force-gauging device can further include electronic circuitry configured to convert the output signals into data indicative of a muscle parameter. The computing device is configured to build a muscle assessment protocol based on one or more patient characteristics and/or user input. The computing device is further configured to execute one or more muscle
(Continued)

assessments via the force-gauging device, receive data from the force-gauging device, and determine one or more muscle measurements for a subject.

16 Claims, 15 Drawing Sheets

(52) U.S. Cl.
CPC ............. *A61B 5/0022* (2013.01); *A61B 5/225* (2013.01); *A61B 2560/0223* (2013.01); *A61B 2560/0475* (2013.01); *A61B 2562/0247* (2013.01)

(58) Field of Classification Search
CPC ... A61B 5/4519; A61B 5/4528; A61B 5/4533; A61B 5/4538; A61B 5/4542; A61B 5/4552; A61B 5/4557; A61B 5/682; A61B 2562/0247; A61B 19/045
USPC ......................................... 600/587, 589, 590
See application file for complete search history.

(56) References Cited

U.S. PATENT DOCUMENTS

| | | | | |
|---|---|---|---|---|
| 5,263,490 | A * | 11/1993 | Hayes | A61B 5/4519 600/554 |
| 8,845,554 | B2 * | 9/2014 | Sarrafzadeh | A61B 5/1107 600/587 |
| 8,905,947 | B2 * | 12/2014 | Annett | A61B 5/228 600/590 |
| 9,517,011 | B2 * | 12/2016 | Kobayashi | A61B 5/01 |
| 10,477,354 | B2 * | 11/2019 | Patel | H04W 4/027 |
| 2006/0241356 | A1 | 10/2006 | Flaherty | |
| 2008/0119763 | A1 | 5/2008 | Wiener | |
| 2013/0281261 | A1 | 10/2013 | Gatherer | |
| 2013/0289401 | A1 | 10/2013 | Colbaugh et al. | |

OTHER PUBLICATIONS

Barlow, S.M. et al.; The Effects of Posteroventral Pallidotomy on Force and Speech Aerodynamics in Parkinson's Disease; Chapter 7; Nov. 21, 2012; 19 pages.

Barlow, Steven M. et al.; Differential Fine Force Control of the Upper and Lower Lips; Journal of Speech and Hearing Research; vol. 29; Jun. 1986; 7 pages.

Barlow, S.M. et al.; Computer Applications in Force Physiology; Handbook of Clinical Speech Physiology; Computer Applications in Orofacial Force Physiology; Chapter 7; 1999; 85 pages.

Barlow, Steven M. et al.; Ramp-and-Hold Force Control in the Upper and Lower Lips: Developing New Neuromotor Assessment Applications in Traumatically Brain Injured Adults; Journal of Speech and Hearing Research; vol. 33; Dec. 1990; 17 pages.

Barlow, Steven M. et al.; Fine Force and Position Control of Select Orofacial Structures in the Upper Motor Neuron Syndrome; Experimental Neurology; vol. 94; Issue 3; 1986; 16 pages.

Barlow, Steven M. et al.; Force Transducer for the Evaluation of Labial, Lingual, and Mandibular Motor Impairments; Journal of Speech and Hearing Research; vol. 26; Dec. 1983; 7 pages.

* cited by examiner

MUSCLE ASSESSMENT SYSTEM AND METHOD

CROSS-REFERENCE TO RELATED APPLICATIONS

This application is a National Stage of International Application No. PCT/US2017/030221 filed Apr. 28, 2017, which is a PCT International Application of U.S. Patent Application No. 62/329,145 filed Apr. 28, 2016. The entire disclosures of the applications referenced above are incorporated by reference.

BACKGROUND

Assessments of muscle force, muscle strength, and voluntary motor control are utilized in the medical field for diagnostic purposes. These assessments can be utilized in a variety of medical disciplines including neurology, geriatric medicine, sports medicine, physical and rehabilitative therapy, medical speech pathology, craniofacial and orthodontic medicine, and diagnostic medicine. These assessments can be used to predict future events such as functional decline, mortality, or morbidity.

SUMMARY

A system and method are described for assessing muscle parameters (e.g., force(s) exerted, force dynamics, strength, voluntary muscle movement, etc.) in a diagnostic or therapeutic environment. The muscle parameter assessment system includes a force-gauging device and a computing device. The force-gauging device includes at least one pressure-sensing component (e.g., transducer, pressure sensor, etc.) configured to respond to a force applied by a subject and produce one or more output signals. The force-gauging device can further include electronic circuitry configured to convert the output signals into data indicative of a muscle parameter. The computing device is configured to build a muscle assessment protocol based on one or more patient characteristics and/or user input. The computing device is further configured to execute one or more muscle assessments via the force-gauging device, receive data from the force-gauging device, and determine one or more muscle measurements for a subject.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. The use of the same reference numbers in different instances in the description and the figures may indicate similar or identical items.

DETAILED DESCRIPTION

Assessments of muscle strength, force dynamics, and voluntary motor control are utilized by medical and dental clinicians, physical therapists, rehabilitation specialists, speech-language pathologists, and neuroscientists. These tests are important tools use for assessing muscle force dynamics among key motor control systems (e.g., hand-digits, orofacial muscles, etc.) involved in daily activities that require skilled movements (manipulation, writing, speech, feeding, gesture) in a wide range of clinical populations across the lifespan who have sustained injuries (e.g., brain stroke, traumatic brain injury) or progressive disease (e.g., Parkinson's disease, amyotrophic lateral sclerosis, cerebellar posterior lobe syndrome, myasthenia gravis) of the nervous system. However, despite the importance of and demand for muscle strength/force tests, there is a lack of real time, integrated assessments and comprehensive assessment protocol tools. Thus, patients are often subject to multiple assessments administered at different times, which can be both tedious and disjointed. Additionally, because most traditional systems for assessing orofacial muscles are stationary or mounted, they can be subject to error due to patient motion or positional artifact.

Accordingly, the present disclosure relates to a system and method for assessing muscle parameters (e.g., force(s) exerted, force dynamics, strength, voluntary muscle movement, etc.) in a diagnostic or therapeutic environment. The muscle parameter assessment system includes a force-gauging device and a computing device. The force-gauging device includes at least one pressure-sensing component (e.g., transducer, pressure sensor, etc.) configured to respond to a force applied by a subject and produce one or more output signals. The force-gauging device can further include electronic circuitry configured to convert the output signals into data indicative of a muscle parameter. The computing device is configured to access a muscle assessment protocol based on one or more patient characteristics and/or user input. The computing device is further configured to execute one or more muscle assessments via the force-gauging device, receive data from the force-gauging device, and determine one or more muscle measurements for a subject.

Figure 1A:
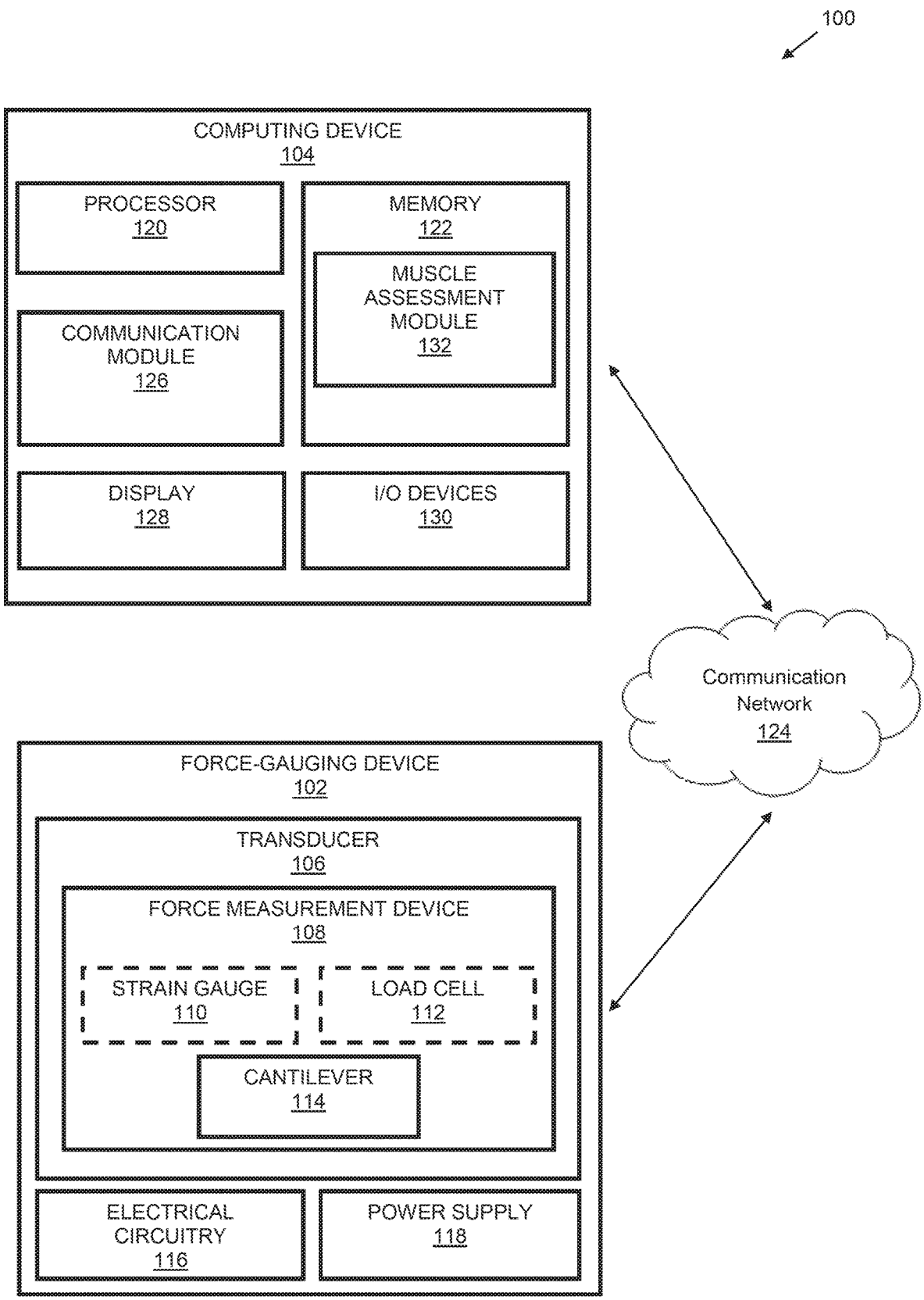
FIG. 1A is a block diagram of a muscle assessment system in accordance with example implementations of the present disclosure.
Figure 1B:
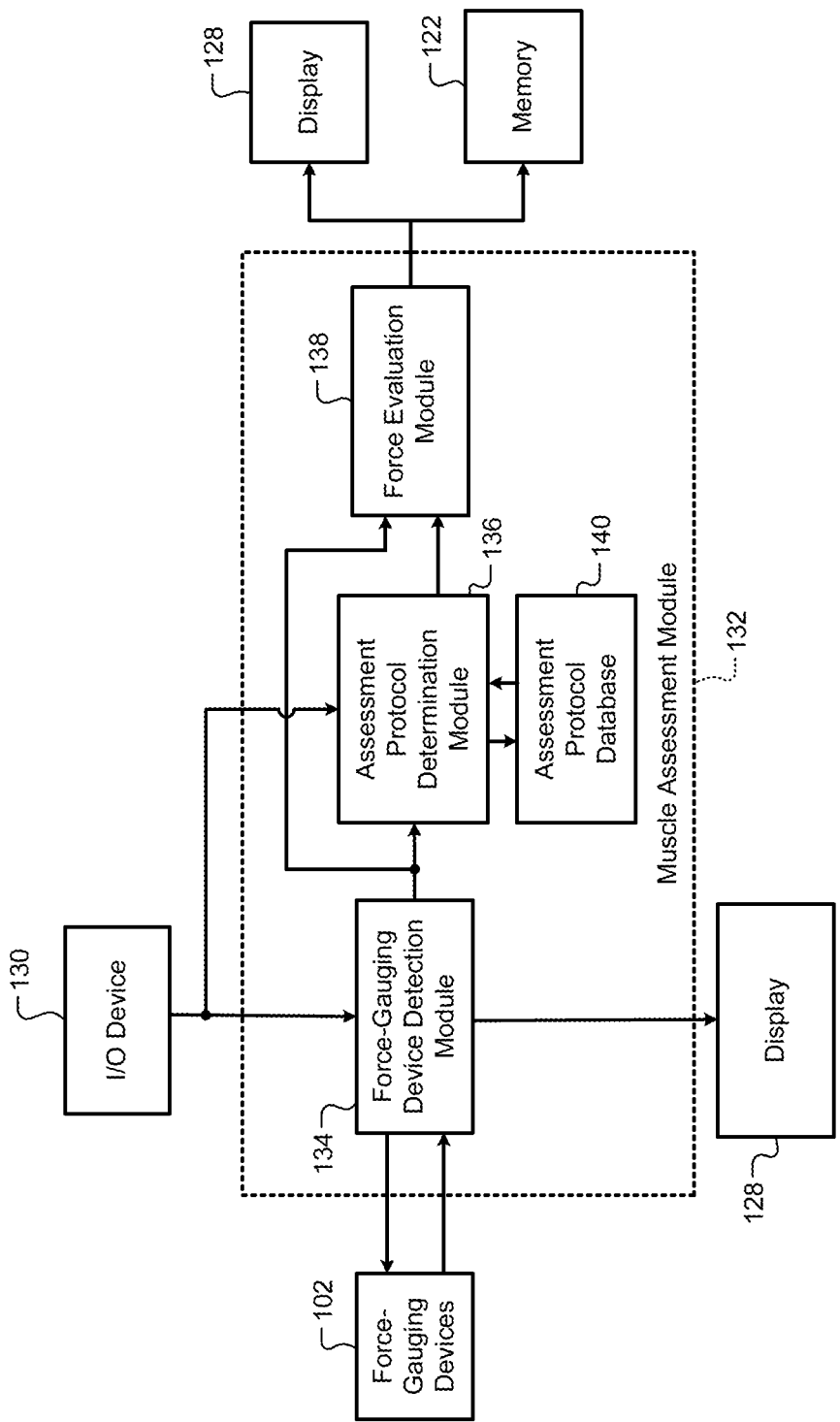
FIG. 1B is an example block diagram illustrating an example muscle assessment module of the muscle assessment system in accordance with an example implementation of the present disclosure.

FIGS. 1A and 1B illustrate a muscle assessment system 100 in accordance with an example implementation of the present disclosure. As shown, the muscle assessment system 100 includes one or more force-gauging device 102 and a computing device 104 communicatively coupled to the pressure-gauging components. The force-gauging devices 102 are configured to measure a muscle parameter (e.g., force(s) exerted, force dynamics, strength, voluntary muscle movement, etc.) of a subject (e.g., a patient). As described below, the one or more force-gauging devices 102 may be integral with the computing device 104 in some implementations or the one or more force-gauging devices 102 may be external to the computing device 104 in other implementations, or a combination thereof The force-gauging device 102 includes one or more pressure-sensing components (e.g., transducers 106, pressure sensors, etc.). The transducer 106 is configured to respond to a force applied by a subject and produce an output signal. In embodiments, the transducer 106 can comprise at least one of a finger transducer, a lip transducer, a tongue transducer, a jaw transducer, and so forth, as described herein. The transducer 106 comprises one or more force measurement devices 108 configured to gauge (e.g., measure) a force (i.e., pressure) applied by a body part (e.g., finger pressure, foot pressure, limb pressure, upper/lower lip pressure, tongue pressure, jaw pressure, lateral oral angle pressure, etc.) of the subject and generate an output signal. In implementations, the force measurement devices 108 can comprise strain gauges (or strain gages) 110, load cells 112, or a combination thereof. The electrical resistance of the strain gauges 110 can vary with the structure of the force-measurement device 108. In example implementations, the strain gauges can be 350 ohm strain gauges. The transducer 106 can further include one or more cantilevers 114 coupled to the strain gauges 110. The cantilevers 114 are configured to provide structural support for the strain gauges 110. The cantilever 114 can be composed of a variety of materials, including, but not necessarily limited to: metal, plastic, and so forth. In example implementations, the cantilevers 114 can be composed of stainless steel. The type (e.g., size and load range) of load cell 112 can also vary with the size and structure of the force measurement device 108. In example implementations, the load cell 112 comprises a subminiature load cell with an optimal load range of 0 to 25 N.

The transducer 106 is coupled to electrical circuitry 116 and a power supply 118 (e.g., battery). The electrical circuitry 116 is configured to condition the output signal (e.g., differential signal generated by the force-gauging devices 102) into data indicative of a muscle parameter. The electrical circuitry 116 and power supply 118 can be configured in a variety of ways based on desired size, communication capabilities, resolution, etc. In some implementations, the electrical circuitry 116 includes a BLUETOOTH® module, a charge-pump regulator with a 3.3V output for supporting a single cell LiPo battery, and a 24-bit analog-to-digital converter (ADC) with an analog front to reduce size and to provide at least 16 bits of resolution. In implementations, the electrical circuitry 116 further includes a small 8-bit PIC chip for general processing. The layout of the electrical circuitry 116 can also be configured in a variety of ways based on size and resolution considerations. In example implementations, the electrical circuitry 116 is configured to be small in size and have high resolution (i.e., low noise). For circuit footprint considerations, the BLUETOOTH® module can be placed on the back of the circuit with the antenna facing to the outside. The ADC can be located on the opposite end to maximize the distance from the antenna. To reduce noise, the microcontroller (MCU) can be located near the ADC. This configuration can also minimize the length of the clock signal distributed from the MCU to the ADC. To reduce size and increase resolution, the regulator can be placed on the other side of the MCU. The electrical circuitry 116 furnishes the muscle parameter data to the computing device 104.

The computing device 104 may be configured in a variety of ways. For example, the computing device 104 may be a server computing device, a desktop computing device, a laptop computing device, an embedded computing device, or the like. In some implementations, one or more elements of the force-gauging device 102 are external to the computing device 104. In other implementations, one or more elements of the force-gauging device 102 are integral with the computing device 104. As shown in FIG. 1A, the computing device 104 includes a processor 120 and a memory 122.

The processor 120 provides processing functionality for the computing device 104 and may include any number of processors, micro-controllers, or other processing systems and resident or external memory for storing data and other information accessed or generated by the computing device 104. The processor 120 may execute one or more modules that implement techniques described herein. For example, the processor 120, in conjunction with one or more modules as described herein, is configured to generate and execute a muscle assessment protocol based on one or more characteristics of a subject and/or user input. For example, one or more modules are configured to cause the processor 120 to select and one or more muscle assessments (e.g., finger pressure, foot pressure, limb pressure, upper/lower lip pressure, tongue pressure, jaw pressure, lateral oral angle pressure, etc.) based on one or more characteristics of a patient and/or user input. The processor can then execute the tests via the one or more transducers 106.

The memory 122 is an example of tangible computer-readable media that provides storage functionality to store various data associated with the operation of the computing device 104, such as the software program and code segments mentioned above, or other data to instruct the processor 120 and other elements of the computing device 104 to perform the steps described herein. Although a single memory 122 is shown, a wide variety of types and combinations of memory may be employed. The memory 122 may be integral with the processor 120, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth.

The computing device 104 is communicatively coupled to transducers 106 over a communication network 124 through a communication module 126 included in the computing device 104. The communication module 126 may be representative of a variety of communication components and functionality, including, but not limited to: one or more antennas; a browser; a transmitter and/or receiver; a wireless radio; data ports; software interfaces and drivers; networking interfaces; data processing components; and so forth.

The communication network 124 may comprise a variety of different types of networks and connections that are contemplated, including, but not limited to: the Internet; an intranet; a satellite network; a cellular network; a mobile data network; wired and/or wireless connections; and so forth.

Examples of wireless networks include, but are not limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; BLUETOOTH® standards promulgated by the BLUETOOTH® Special Interest Group; and so on. Wired communications are also contemplated such as through universal serial bus (USB), Ethernet, serial connections, and so forth.

The system 100 may include a display 128 to display information to a user of the computing device 104. In embodiments, the display 128 may comprise an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. In an implementation, the processor 120 may be configured to provide data indicative of a muscle parameter and/or a muscle measurement to the display 128 for display purposes.

As shown in FIG. 1A, the muscle assessment system 100 may include one or more input/output (I/O) devices 130 (e.g., a keypad, buttons, a wireless input device, a thumbwheel input device, a trackstick input device, a touchscreen, and so on). The I/O devices 130 may include one or more audio I/O devices, such as a microphone, speakers, and so on.

As shown in FIG. 1A, the computing device 104 includes a muscle assessment module 132 which is storable in the memory 122. The muscle assessment module 132 is executable by the processor 120. The muscle assessment module 132 is representative of functionality to perform a real time muscle assessment in a medical care environment. For example, the muscle assessment module 132 is representative of functionality to perform one or more protocols of muscle parameter assessments on a subject (e.g., patient). The module 132 is configured to access and/or build a protocol of muscle parameter assessments based on one or more patient characteristics and/or user (e.g., caregiver, medical personnel, therapist, etc.) input. The module 132 may then execute the protocol of muscle parameter assessments and determine at least one muscle parameter measurement for the subject based on the muscle parameter assessments. The system 100 may be utilized to perform comprehensive, real time muscle assessments on a patient within a medical care environment, such as a hospital environment, a medical clinic, a rehabilitation environment, a home environment, or the like.

The muscles assessment module 132 is configured to cause the processor 120 to access one or assessment protocols for patients that are storeable in memory 122. In implementations, the muscles assessment module 132 can cause the processor 120 to identify one or more connected force-gauging devices 102 via the communication network 124. In other implementations, a user can manually select devices 102 for the muscle assessment system 100 to connect to. For example, the muscles assessment module 132 can cause the processor to display a list of available force-gauging devices 102 via the display 128. Using the muscle assessment system 100, the user can then select one or more devices 102 to connect to. The processor 120 is configured to determine a protocol of assessments that can be executed with the connected force-gauging device 102. For example, the processor 112 can cause the force-gauging device 102 to generate data representing a muscle parameter (e.g., force(s) exerted, force dynamics, strength, voluntary muscle movement, etc.).

FIG. 1B illustrates an example muscle assessment module 132 in accordance with the present disclosure. As shown, the muscle assessment module 132 includes a force-gauging device detection module 134, an assessment protocol determination module 136, and a force evaluation module 138.

The muscle force-gauging device detection module 134 detects the force-gauging devices 102 via the communication network 124. For instance, the force-gauging device detection module 134 detects the force-gauging devices 102 based upon respective signals provided to the force-gauging device detection module 134. The force-gauging device(s) 102 may initiate a communication link via the communication network 124 by transmitting one or more synchronization signals to the force-gauging device detection module 134. The force-gauging device detection module 134 can respond with a synchronization signal to establish the communication link. Additionally, one or more users can cause the force-gauging device detection module 134 to detect one or more force-gauging devices 102 based upon a selection by the users. In this example, the force-gauging device detection module 134 causes display of the detected force-gauging device(s) 102 at the display 128. A user can use an I/O device 130 to select the one or more force-gauging device(s) 102 to establish a communication link with.

The assessment protocol determination module 136 receives one or more force-gauging device detection signals indicative of the force-gauging devices detected by the force-gauging device detection module 134. Based upon the received signals, the assessment protocol determination module 136 accesses (i.e., selects) and/or builds one or assessment protocols for the patient utilizing the connected force-gauging devices 102. The assessment protocol may be accessed and/or built from one or more predefined assessment protocols retained in an assessment protocol database 140. For instance, the assessment protocol determination module 136 selects one or more muscle assessments for the patient that can be performed by the patient via the identified force-gauging device 102.

The assessment protocol determination module 136 accesses the assessment protocol database 140 that includes predefined assessment protocols that correspond to the respect force-gauging device 102 connected with the force-gauging devices 102. In one or more implementations, the assessment protocol database 140 retains predefined, or predetermined, assessment protocols that correspond to respective force-gauging devices 102 and/or patient characteristics. The patient characteristics can be provided and/or selected by a user through the I/O device 130. For instance, based upon the force-gauging device 102 in communication with the force-gauging device detection module 134, the assessment protocol determination module 136 accesses the assessment protocol database 140 to obtain the corresponding assessment protocol.

Additionally, the assessment protocol determination module 136 can receive one or more assessment protocols selected by a user based upon the patient and/or the force-gauging devices 102 connected with the muscle assessment system 100. For instance, a user can select the assessment protocol based upon signals indicative of the selected assessment protocol from the I/O devices 130. In one or more implementations, the assessment protocol provides target force parameters, or values, corresponding to the patient, and the patient exerts a force via the force-gauging device 102.

The force evaluation module 138 receives signals indicative of the exerted force and compares the exerted force to the target force parameters. In one or more implementations, as described herein, the force evaluation module 138 applies one or more suitable processes to transform the data into one or more muscle measurements. For instance, the force evaluation module 138 applies one or more models to the data indicative of the exerted forces to generate corresponding output muscle measurement because the exerted force is indicative of a muscle parameter used to exert the force. The force evaluation module 138 can cause the display 128 to display the target force parameters and the corresponding exerted force. Display of the target force parameters and the corresponding exerted force at the display 128 can provide feedback to the patient regarding how much force the patient is exerting relative to the target force parameters. Additionally, the force evaluation module 138 provides the signals indicative of the exerted force to the memory 122. For instance, a user, such as medical personnel, can access the stored data to compare current exerted force data to previously measured exerted force data.

Figure 2:
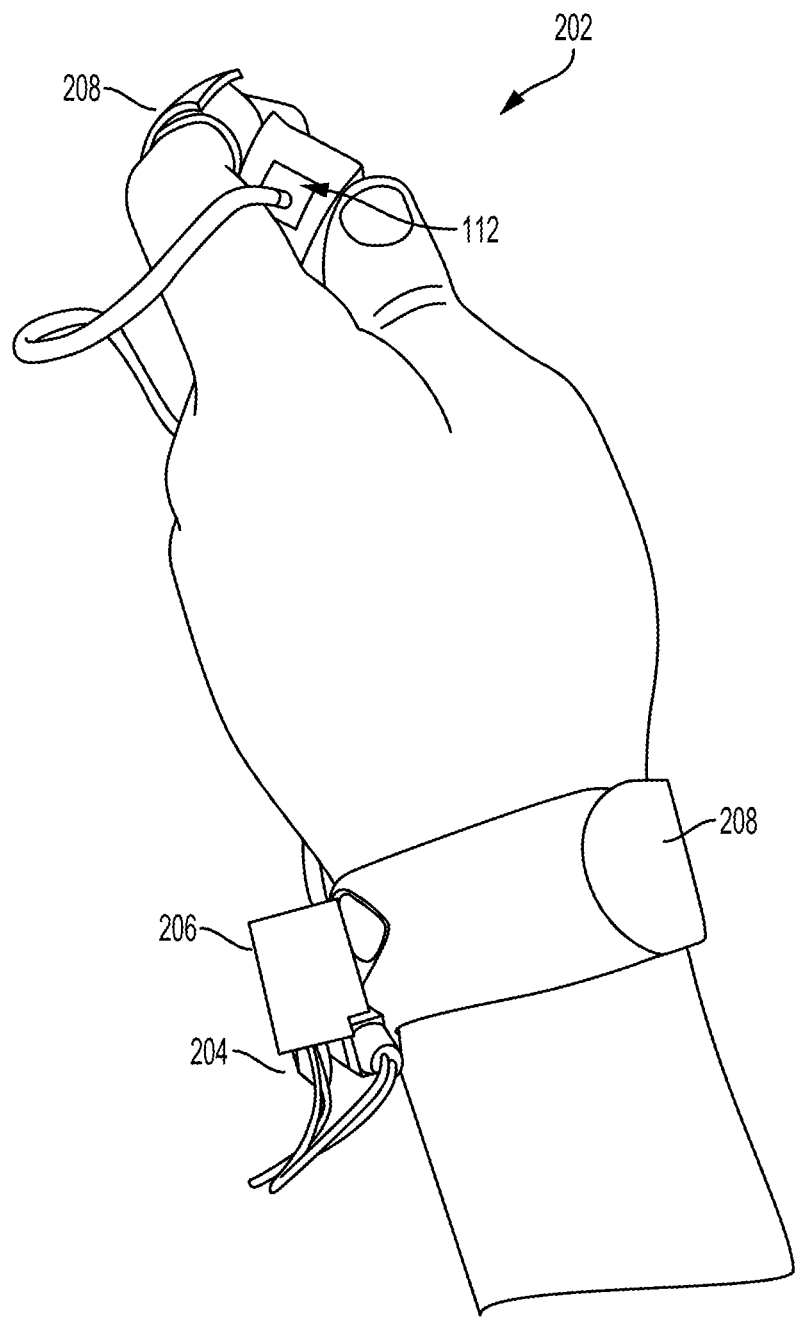
FIG. 2 is a perspective view illustrating a finger transducer device in accordance with example implementations of the present disclosure.
Figure 3:
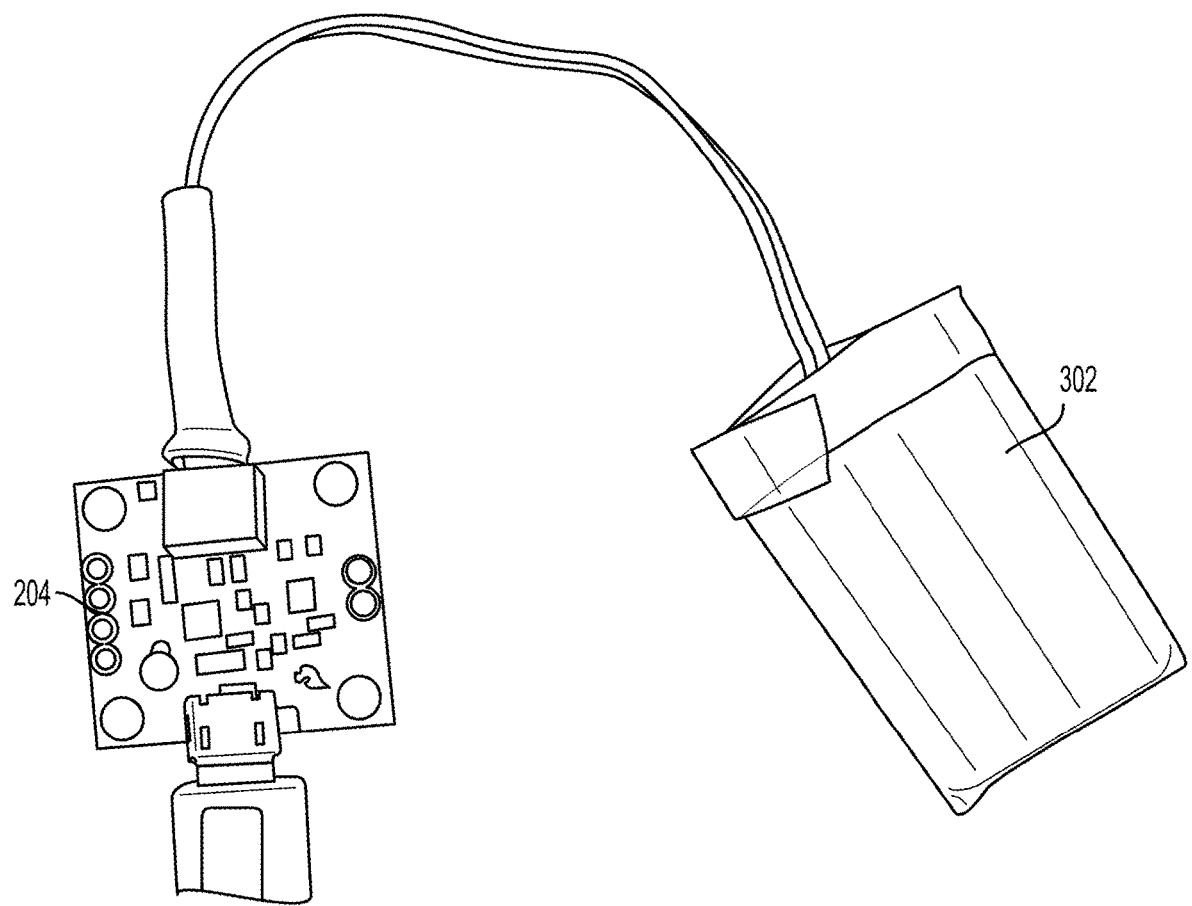
FIG. 3 is a top view illustrating electronic circuitry operable to facilitate a finger transducer device in accordance with example implementations of the present disclosure.
Figure 4:
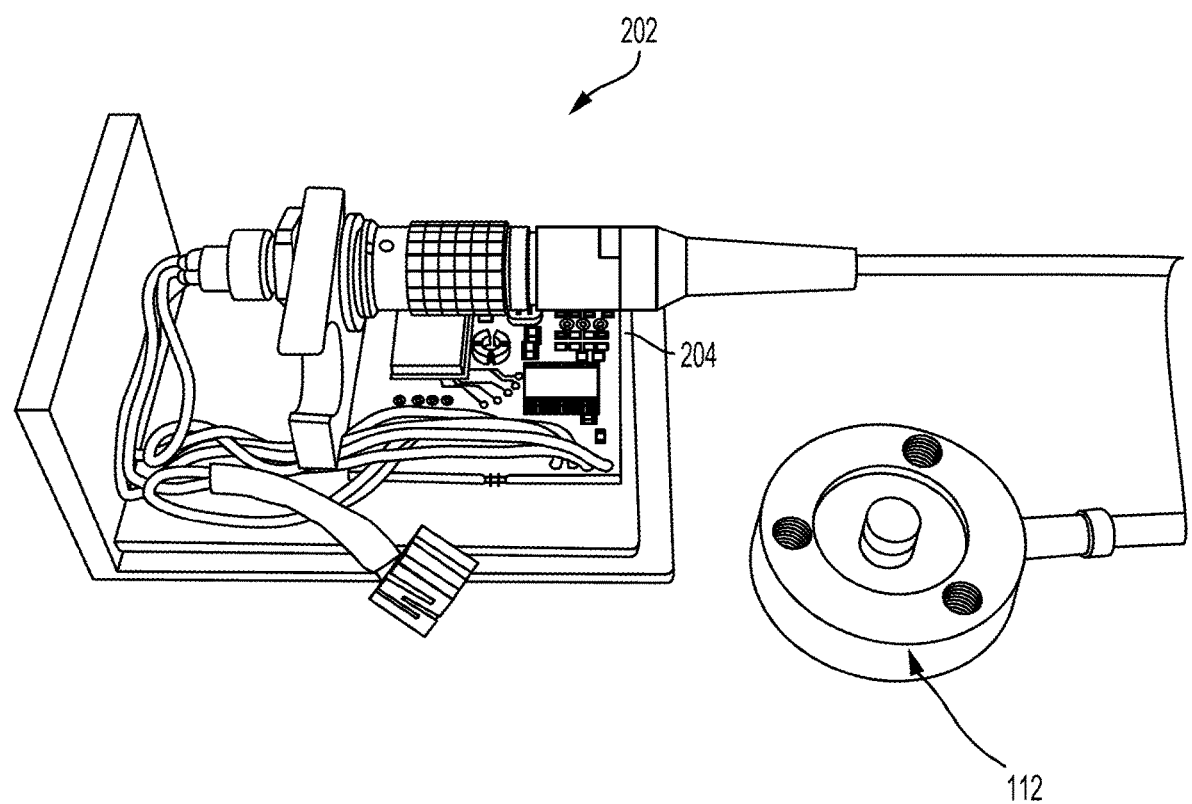
FIG. 4 is another perspective view illustrating a finger transducer device in accordance with example implementations of the present disclosure.

As shown in FIGS. 2 through 8, the system 100 can include a variety of force-gauging devices 102 configured to communicate with the computing device 104 utilizing the techniques described herein. In some implementations, one or more of the force-gauging devices 102 can comprise a finger transducer device 202, as illustrated in FIG. 2. The finger transducer device 202 can include a load cell 112 configured to gauge a force applied by a hand digit (i.e., finger) and generate an output signal. The finger transducer device 202 can further include electrical circuitry 204 configured to condition the output signal into data indicative of digit muscle parameter (e.g., force(s) exerted, force dynamics, strength, voluntary muscle movement, etc.). In implementations, the electrical circuitry 204 can be enclosed in a housing 206. The electrical circuitry 204 is further configured to allow the finger transducer device 202 to communicate with the computing device 104 via the communication network 124. For example, the electrical circuitry 204 enables the processor 120 to identify the presence of the finger transducer device 202, and enables transfer of data between the finger transducer device 202 and the processor 120, as described herein. The finger transducer device 202 can further include one or more straps 208 configured to removably attach the device 202 to a finger, hand, and/or arm. The straps 208 can be comprised of a variety of materials including, but not necessarily limited to: a fastener material (i.e., Velcro®), elastic, and so forth. The finger transducer 202 further includes a power supply (e.g., battery 302) configured to generate power for the device 202, as illustrated in FIG. 3.

Figure 5:
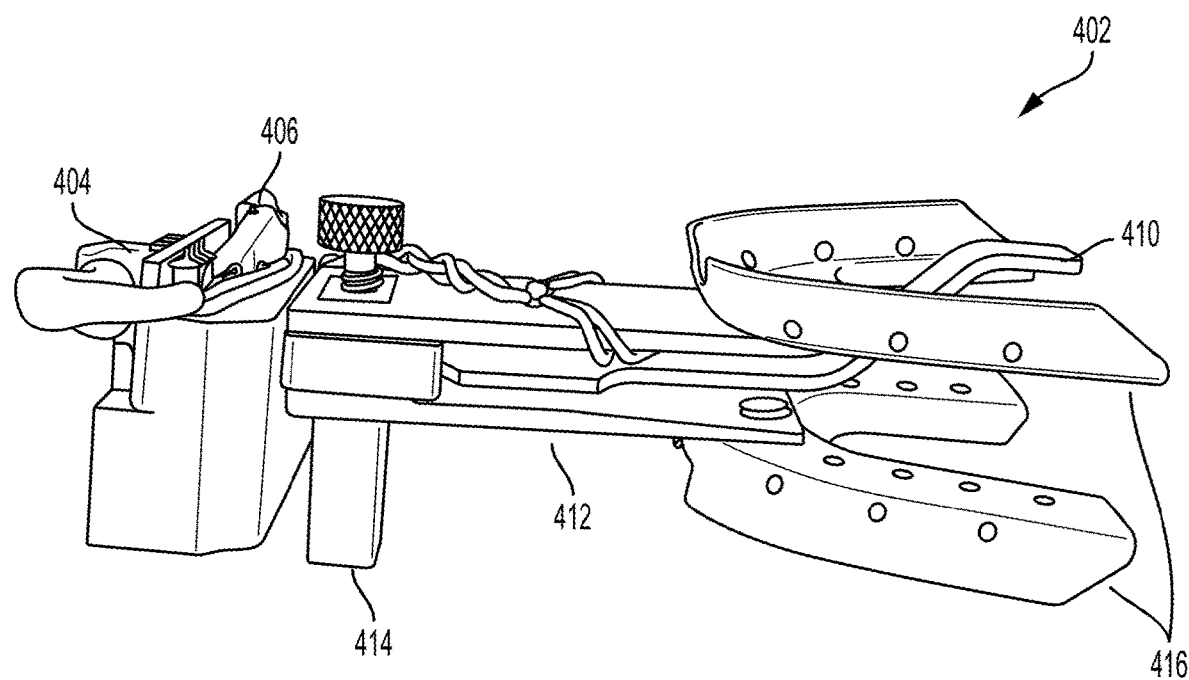
FIG. 5 is a side view illustrating an orofacial transducer device in accordance with example implementations of the present disclosure.
Figure 6:
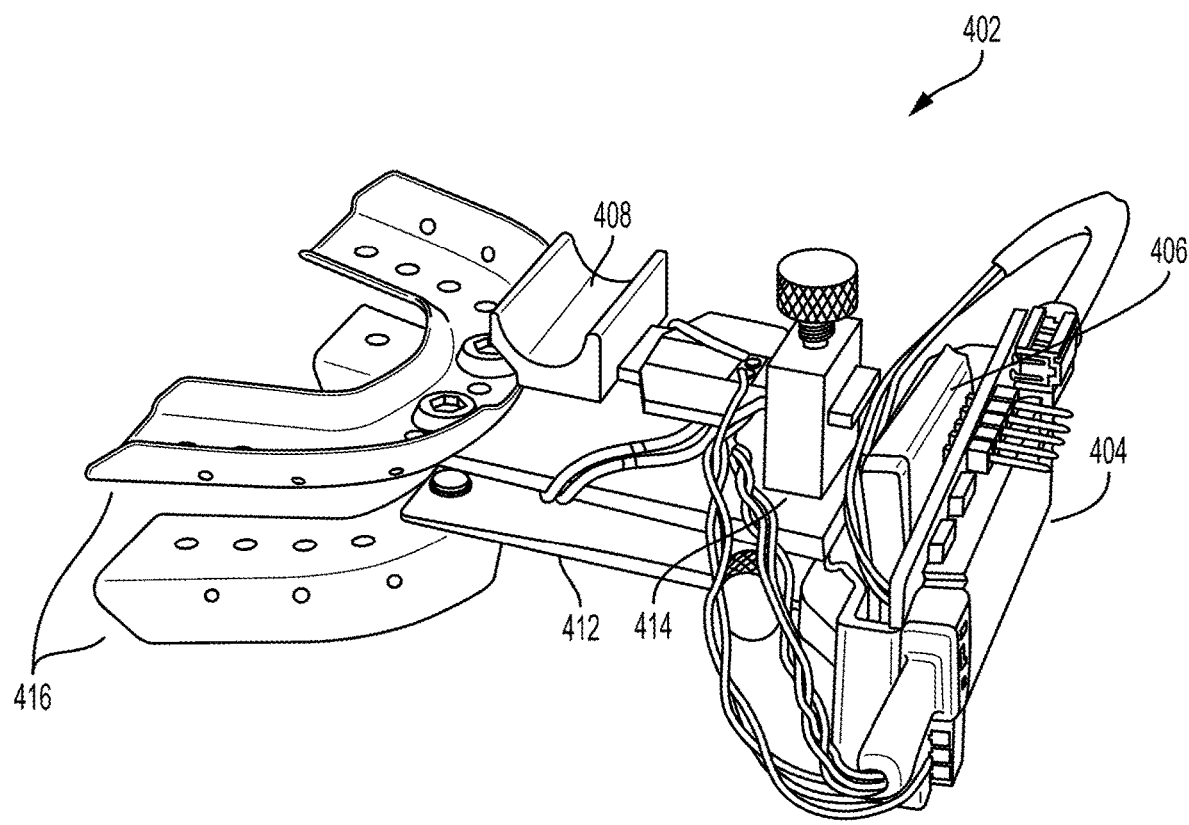
FIGS. 6 and 7 are perspective views illustrating an orofacial transducer device in accordance with example implementations of the present disclosure.
Figure 7:
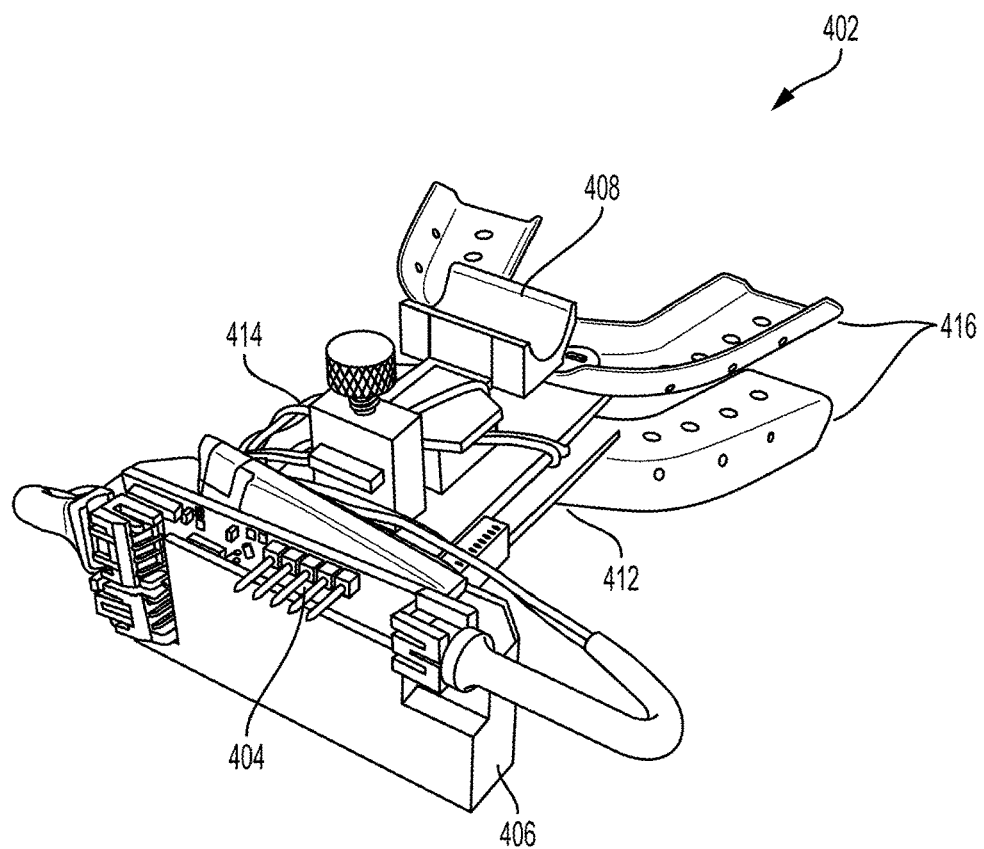

In some implementations, one or more of the force-gauging devices 102 can comprise an orofacial transducer device 402, as illustrated in FIGS. 5 through 7. The orofacial transducer device 402 can include one or more strain gauges 110 configured to gauge a force applied by a by a mouth and/or facial muscle (e.g., upper/lower lip pressure, tongue pressure, jaw pressure, lateral oral angle pressure, etc.) and generate an output signal. The orofacial transducer device 402 can further include electrical circuitry 404 configured to condition the output signal into data indicative of at least one orofacial muscle force parameter (e.g., force(s) exerted, force dynamics, strength, voluntary muscle movement, etc.). In implementations, the electrical circuitry 404 can be enclosed in a housing. The orofacial transducer device 402 further includes one or more cantilevers 114 configured to support the strain gauges 110 and/or the electrical circuitry 404. The orofacial transducer device 402 further includes a power supply (e.g., battery 406) configured to generate power for the device 402. In implementations, the battery 406 and/or the electrical circuitry 404 can be coupled to one or more of the cantilevers 114, as described below.

The orofacial transducer device 402 can include a variety of types transducers 106 configured to measure force(s) exerted by and/or force dynamics of one or more orofacial muscles. In some implementations, the orofacial transducer device 402 can include one or more lip transducers 408 configured to measure applied lip force from the upper and/or lower lip. The lip transducer 408 can comprise a lip rest and one or more strain gauges 110 coupled to a cantilever 114. The strain gauges 110 are configured to respond to a force applied by the lips (e.g., upper lip pressure, lower lip pressure, lateral oral angle pressure, etc.) and generate an output signal representing said force. In some implementations, the orofacial transducer device 402 can include a tongue transducer 410 configured to measure applied tongue force. The tongue transducer 410 can comprise one or more strain gauges 110 coupled to a cantilever 114. The strain gauges 110 are configured to respond to a force applied by the tongue (e.g., tongue pressure) and generate an output signal representing said force. The orofacial transducer device 402 can also include a jaw transducer 412 configured to measure applied jaw force. The jaw transducer 412 can comprise one or more strain gauges 110 coupled to a cantilever 114.

The strain gauges 110 are configured to respond to a force applied by the jaw (e.g., jaw pressure) and generate an output signal representing said force. The shape of the jaw transducer 412 is significant both in terms of its relationship to the other transducer devices (e.g., lip transducer 408, tongue transducer 410, etc.), and in terms of its relationship to mouth size and shape. In example implementations, the jaw transducer can comprise a U-shape formed from two cantilevers 114. The U-shaped base can serve as a base to hold the additional transducer devices. The U-shaped transducer can also provide a comfortable biting distance for the patient, while still providing easy access to the mouth for the tongue transducer with relatively no interference.

In implementations, the orofacial transducer device can also include a height adjustment arm 414, as illustrated in FIGS. 5 through 10. The height adjustment arm 414 is coupled to one or more of the cantilevers 114 and is configured to raise and/or lower the height of the cantilevers 114. In some implementations, the height adjustment arm 414 is disposed between to the lip transducer 408 and the base formed by the jaw transducer 412. The height adjustment arm 414 can include a slot for the cantilever of the lip transducer 410 to slide in and a hole for an adjustable fastener (e.g., bolt, screw, etc.) to lock the cantilever 114 in place. The jaw transducer 412 can include another adjustable fastener to allow for vertical height of adjustment of the arm 414. The height adjustment arm 414 allows for both vertical and lateral movement of the lip transducer 408, permitting the user to position the lip transducer 408 in a position that is comfortable for each patient. The height adjustment arm 414 can be composed of a variety of materials, including, but not necessarily limited to: metal, plastic, and so forth. In example implementations, the height adjustment arm 414 can be composed of stainless steel.

The orofacial transducer device 402 can further include a mouth tray 416 for holding the patient's mouth in place as well as positioning a patient's maxillary and mandibular dentition, as illustrated in FIGS. 5 through 9. As described below, the mouth tray 416 can further include dental retaining material 418 for forming to a patient's dental configuration. The mouth tray 416 can be formed in a variety of sizes (e.g., small, medium, large, etc.) to accommodate different mouth sizes and shapes. The mouth tray 416 can be composed of a variety of materials, including, but not necessarily limited to: metal, plastic, and so forth. In example implementations, the mouth tray 416 can be manufactured of stainless steel. The mouth tray 416 can be removably attached to a cantilever 114 via one or more removable fasteners (e.g., bolts, screws, snap couplers, etc.). In implementations, the mouth tray 416 can be removably attached to the cantilevers 114 of the jaw transducer 412.

The lip transducer 408, tongue transducer 410, and/or jaw transducer 412 are coupled to the electrical circuitry 404 and/or the battery 406. The battery 406 and/or the electrical circuitry 404 can be coupled to one or more of the cantilevers 114. In some implementations, the battery 106 and/or electrical circuitry 404 are supported by the cantilevers 114 of the jaw transducer 412, as illustrated in FIGS. 5 through 10.

Figure 8:
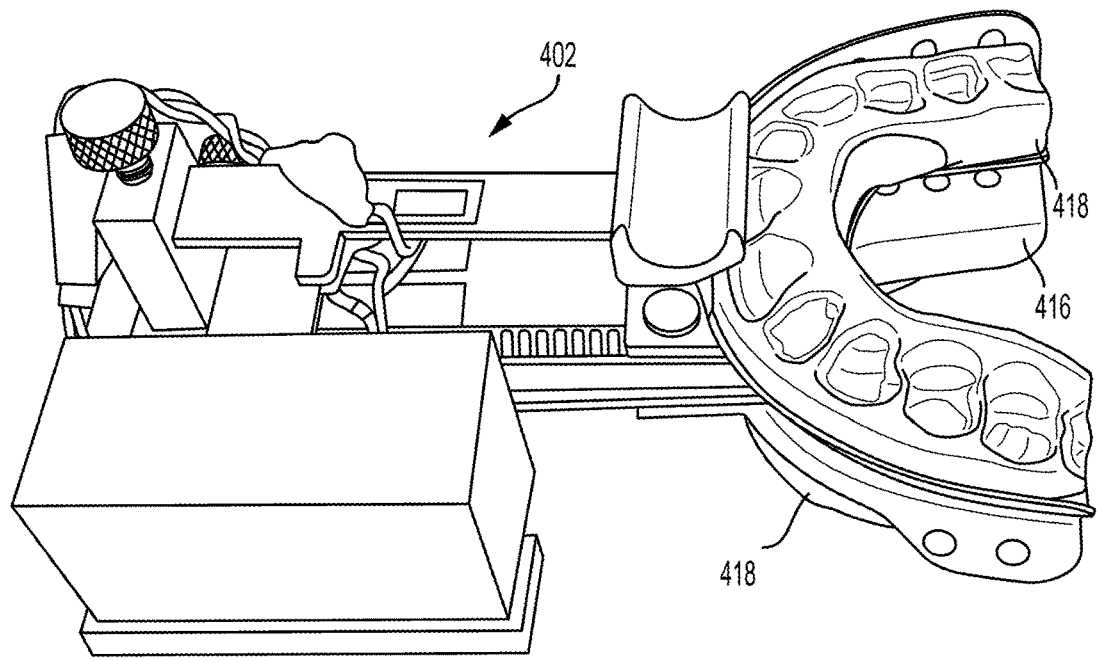
FIGS. 8 and 9 are perspective views illustrating an orofacial transducer device employing dental retaining material in accordance with example implementations of the present disclosure
Figure 9:
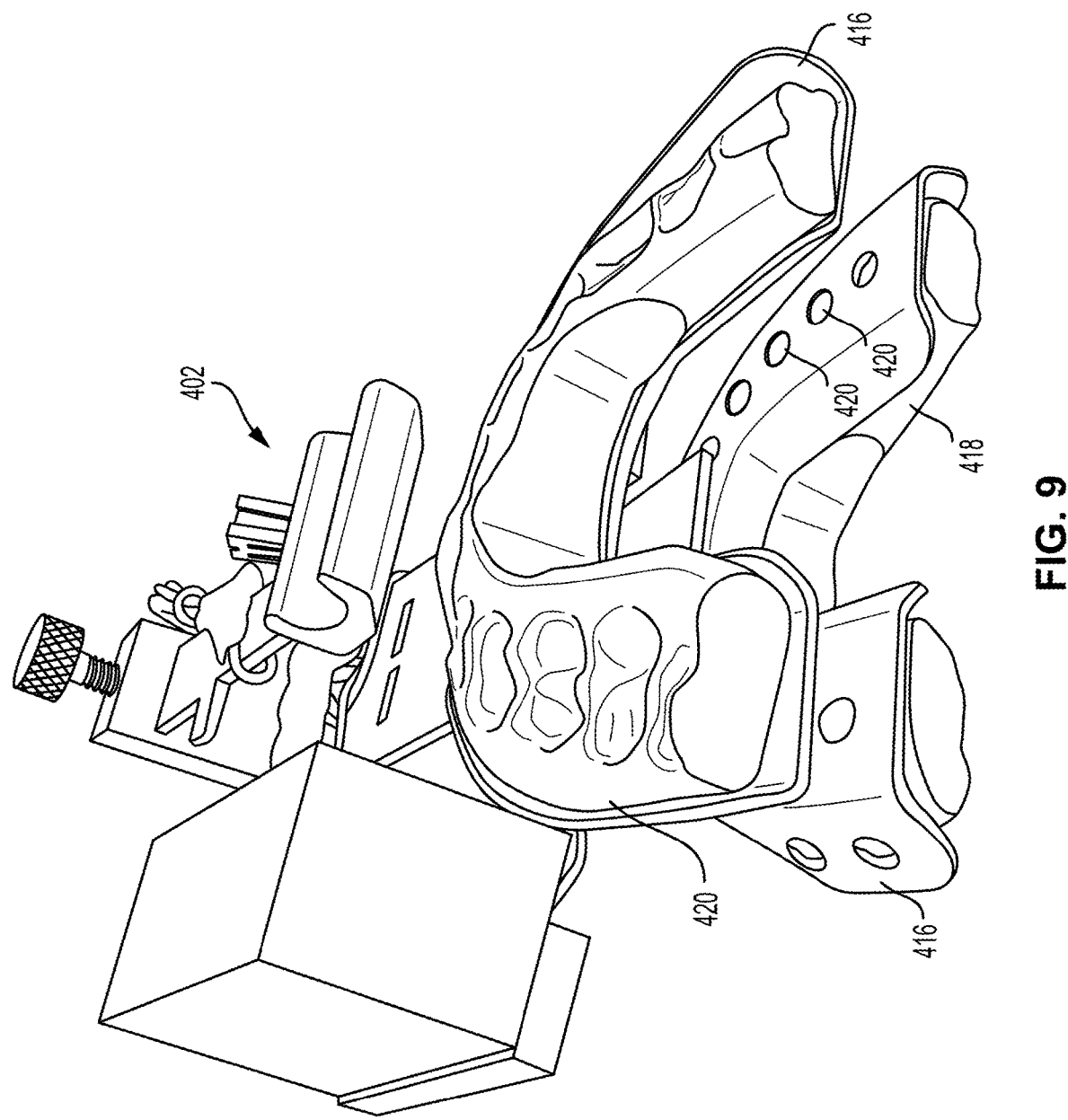

As shown in FIGS. 8 and 9, dental retaining material 418 can be employed by the mouth tray 416 to provide additional comfortability to the patient. For example, the dental retaining material 418 can conform to the patient's dental configuration. The dental retaining material 418 includes a suitable impression material, such as impression compounds. For instance, the impression material may be an alginate material, a silicone material, a polyether material, a hydrocolloid material, or the like. In various implementations, the dental retaining material 418 is applied to the mouth tray. A force is applied to the dental retaining material 418 such that a portion of the dental retaining material 418 is received within one or more apertures 420 defined within the mouth tray 416. The received portions of the dental retaining material 418 adheres to the apertures 420 such that the mouth tray 416 retains the dental retaining material 418.

Figure 10:
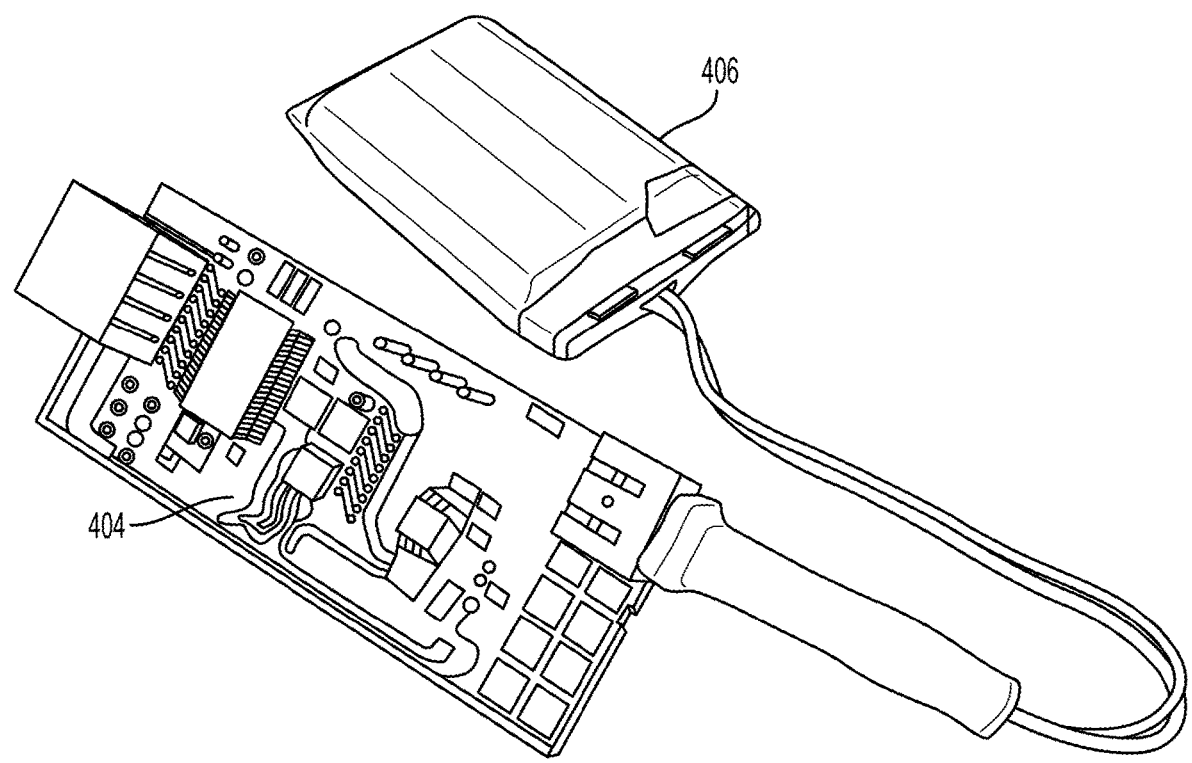
FIG. 10 is a perspective view illustrating electronic circuitry operable to facilitate an orofacial transducer device in accordance with example implementations of the present disclosure.

FIG. 10 illustrates example electrical circuitry 404 operable to facilitate the orofacial transducer device 402 in accordance with the present disclosure. The electrical circuitry 404 is configured condition the output signals received from the lip transducer 408, tongue transducer 410, and/or jaw transducer 412 into a data package that is indicative of at least one muscle parameter (e.g., force(s) exerted, force dynamics, strength, voluntary muscle movement, etc.). In implementations, the electric circuitry 404 can be integrated for all orofacial transducers (lip transducer 408, tongue transducer 410, and/or jaw transducer 412), and all orofacial transducers can be head-referenced, so that the forces generated by each transducer are anatomically referenced to the facial skeleton. This integrated transducer design can reduce or eliminate signaling errors due to motion or positional artifact. The electrical circuitry 404 is further configured to allow the orofacial transducer device 402 to communicate with the computing device 104 via the communication network 124. For example, the electrical circuitry 404 enables the processor 120 to identify the presence of the orofacial transducer device 402, and enables transfer of data between the orofacial transducer device 402 and the processor 120, as described herein.

It is to be understood that while external force-gauging devices are illustrated in 5 through 10, the use of external force-gauging devices are offered by way of example only and are not meant to be restrictive of the present disclosure. In other implementations, the muscle assessment system 100 can include one or more force-gauging devices 102, or elements thereof, that are integral with the computing device 104. For example, one or more of the force-gauging devices 102 can comprise a pressure sensor that is internal to the computing device 104.

Figure 11:
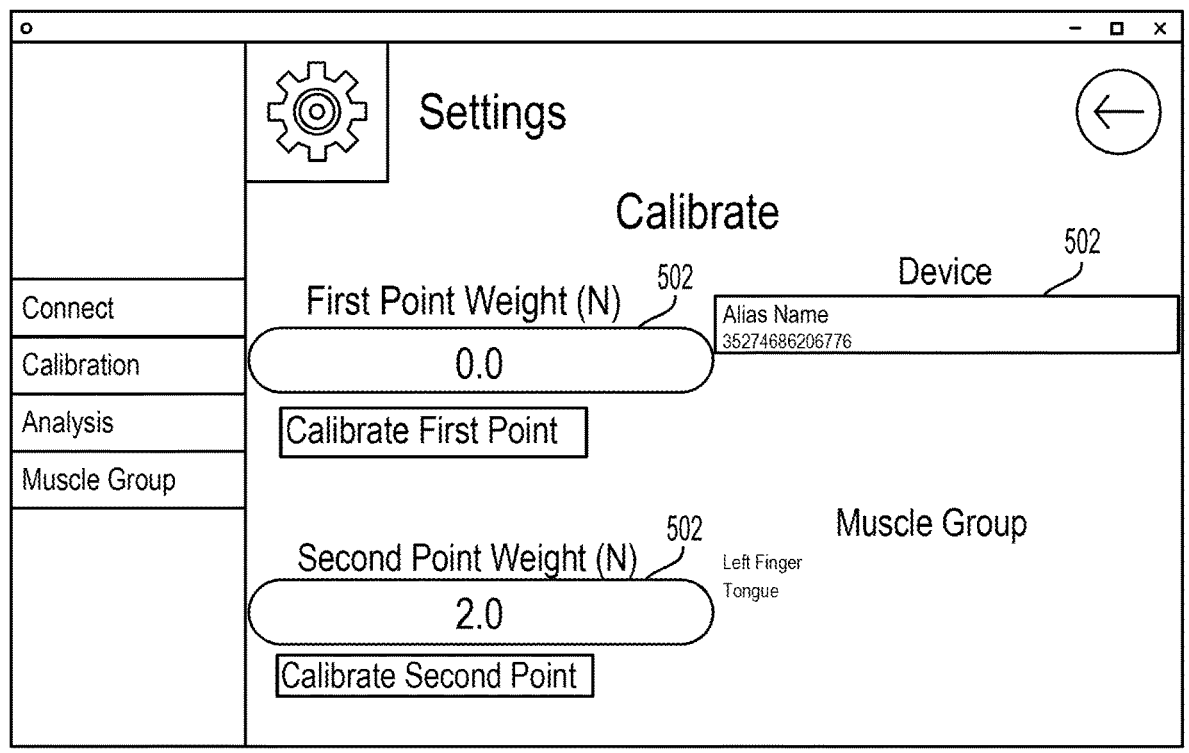
FIGS. 11 through 13 illustrate example screen shots in accordance with example implementations of the present disclosure.

Once the processor 120 identifies the presence of a force-gauging device 102 (e.g., finger transducer device 202, orofacial transducer device 402, etc.), the muscle assessment module 132 can cause the processor 120 to calibrate the force-gauging device 102, as illustrated in FIG. 11, based on input from user interfaces 502. In implementations, a two-point calibration can be performed on connected devices 102.

Figure 12:
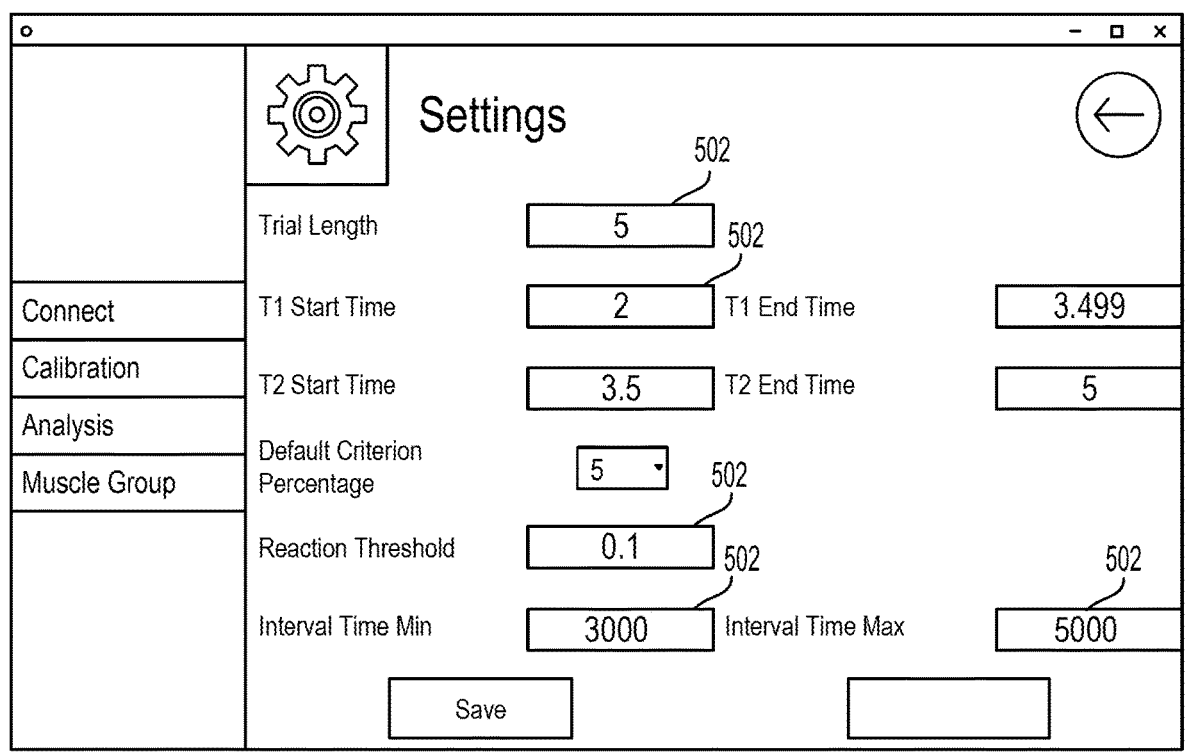
Figure 13:
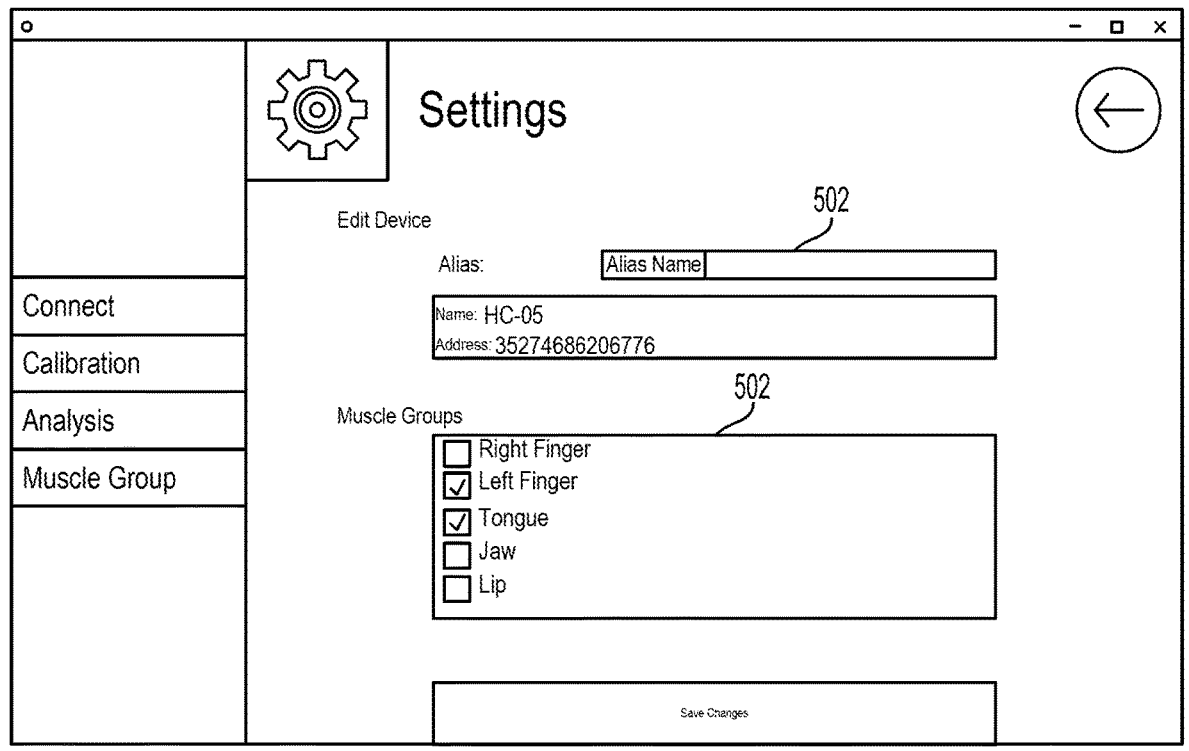

The muscle assessment module 132 is configured to cause the processor 120 to build one or assessment protocols for the patient utilizing the connected force-gauging devices 102, as described above with respect to FIG. 1B. For example, the muscle assessment module 132 can select one or more muscle assessments for the patient that can be executed by the identified force-gauging device 102. In some implementations, a user can add one or more assessments to a protocol using the display 128 and the I/O devices 130. For example, the muscle assessment module 132 can cause the processor 120 to display a variety of assessment criteria via the display 128. Using the user interfaces 502, the user can select or input one or more assessment criteria when prompted by the display 128, as illustrated in FIGS. 11 through 13. Assessment criteria can comprise a variety of testing parameters including, but are not necessarily limited to: muscle groups to be tested, trial length, trial start time/end time, default criterion percentage, reaction threshold, interval time minimum/maximum, and so forth. The user can build the assessment protocol tailored to the patient based on patient characteristics. The characteristics may include, but are not limited to: age, gender, weight, body type/dimensions, diagnoses, able-bodied, physical restrictions (e.g., missing limbs), and/or facial deformities. It is to be understood that the use of user input to build the assessment protocol is offered by way of example only and is not meant to be restrictive of the present disclosure. In other embodiments, the muscle assessment system 100 may apply one or more algorithms and/or machine learning techniques to generate an assessment protocol (i.e., based on patient characteristics).

In implementations, the muscle assessment module 132 can cause the processor 120 to execute the assessment protocol via the connected force-gauging devices 102. The processor 120 can cause the force-gauging devices 102 to respond to a force applied by a patient, as described above. For example, the processor 120 can cause the force-gauging devices 102 to respond to a force applied by a body part (e.g., finger pressure, foot pressure, limb pressure, upper/lower lip pressure, tongue pressure, jaw pressure, lateral oral angle pressure, etc.). The force-gauging devices 102 can generate an output signal corresponding to the applied force and can generate a package (e.g., packet) of data indicative of at least one muscle parameter (e.g., force(s) exerted, force dynamics, strength, voluntary muscle movement, etc.). In one or more implementations, the force-gauging devices 102 are configured to generate data indicative of fine force regulation (i.e., a range from 0 to 100% of maximum voluntary contraction). The processor 120 can transmit the data to the computing device 104 via the communication network 124.

Figure 14:
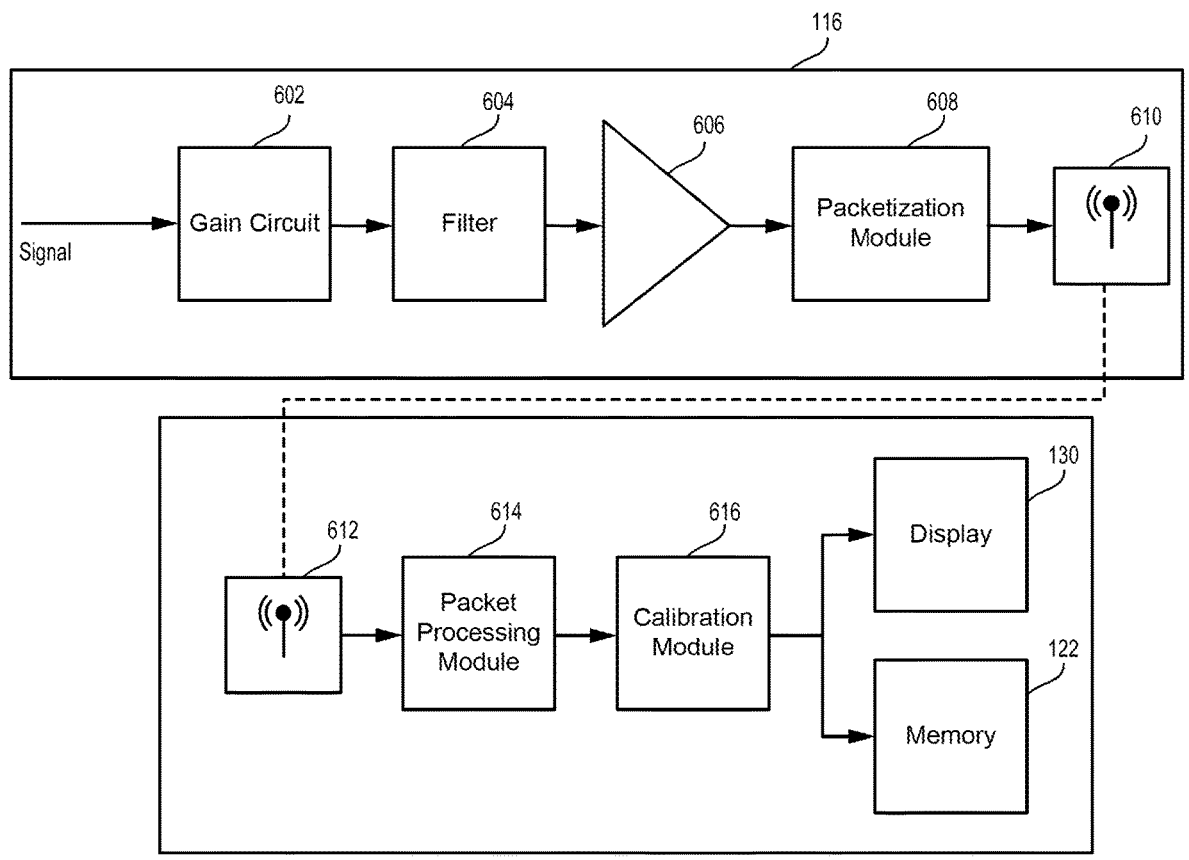
FIG. 14 is a block diagram illustrating electronic circuitry employed by the muscle assessment system in accordance with example implementations of the present disclosure.

FIG. 14 illustrates an example block diagram of the electrical circuitry 116 and the muscle assessment module 132. In one or more implementations, the electrical circuitry 116 includes a gain circuit 602, a filter 604, a data converter 606, a packetization module 608, and a transmitter 610. In one or more implementations, the muscle assessment module 132 includes a receiver 612, a packet processing module 614, and a calibration module 616.

The gain circuit 602 receives an input signal, such as a differential signal, representing an exerted force. The gain circuit 602 increases a characteristic (i.e., power, amplitude) of the input signal and generates an output signal indicative of the adjusted characteristic. The filter 604 receives the adjusted signal and applies a filter to generate a filtered signal. For instance, the filter 604 may be a sine filter that removes frequency characteristics of the adjusted signal above a given cutoff frequency. The data converter 606 receives the filtered signal and generates a converted signal indicative of the filtered signal. For instance, the data converter 606 may be an analog-to-digital converter that converts the filtered signal to a digital signal. The packetization module 608 receives the converted signal and generates, or encapsulates, one or more data packets according to a communication protocol for transmission via the communication network 124. In some instances, the packetization module 608 includes a timestamps within the one or more data packets. The transmitter 610 then transmits the data packets via the communication network 124.

The receiver 612 receives the data packets and provides the received data packets to the packet processing module 614. The packet processing module 614 processes, or de-capsulates, the data packets to obtain the data indicative of the exerted force and/or timestamps encoded within the data packets. The calibration module 616 calibrates the data indicative of the exerted force and generates an output based upon the calibrated data. For instance, the calibration module 616 associates the data indicative of the exerted force with corresponding data within the assessment protocol. The calibration module 616 can associate the data indicative of the exerted force with the corresponding data within the assessment protocol based upon the timestamp data. As described above, the calibration module 616 provides the calibrated data to the display 128 and/or the memory 122.

The muscle assessment module 132 can cause the processor 120 to receive the data indicative of a muscle parameter form the force-gauging devices 102 and generate at least one output muscle measurement. For example, the processor 120 (i.e., force evaluation module 138) can execute one or more processes, or algorithms, to transform the data into one or more muscle measurements. In an example implementation, the processes represent data models that can be applied to the data such that the data represents muscle measurements. For instance, the processor 120 can utilize one or more processes, or data models, to generate the following output muscle measurements:

Force reaction time with simple linear regression
Force rise time with simple linear regression
Force slope (10-90% intercepts during recruitment/decruitment) with simple linear regression
Force derivative (time series) for rate of force change
Force derivative maxima during recruitment by force target by muscle tested with simple linear regression
Force peak during recruitment by trial by force target by muscle tested with simple linear regression
Force hold phase (mean) during two successive 1.5 second periods from 3 to 5 seconds with simple linear regression
Force standard deviation during two successive 1.5 second periods from 3 to 5 seconds with simple linear regression
Individual force trials display by force target and muscle tested
Mean force (with 95% and 99% confidence intervals) time series by force target and muscle tested
Fourier Transform (power spectrum) by force trial by force target by muscle tested
Principal Frequency Components (f0, f1, f2) with simple linear regression
Criterion Percentage–quantitative metric of % time patient's force within +/–target force with simple linear regression In implementations, the received data and/or the output muscle measurements are storable in memory 122. The received data and/or the output muscle measurements may also be presented via the display 128, or the like.

Figure 15:
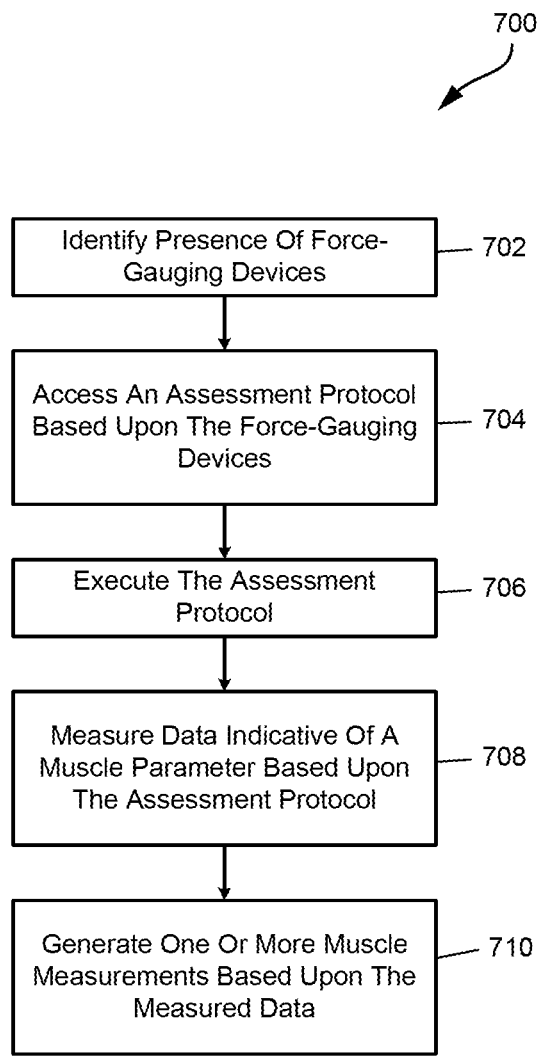
FIG. 15 is a flow diagram illustrating an example method for assessing a muscle parameter in accordance with the present disclosure.

FIG. 15 illustrates an example process 700 for performing a muscle assessment of a patient utilizing the muscle assessment system 100 described above. As shown in FIG. 15, the presence of one or more force-gauging devices is identified (Block 702). As described above, the muscle assessment system 100 is configured to identify the presence of one or more force-gauging devices 102. In some implementations, the muscle assessment module 132 can cause the processor 120 to automatically detect and connect to the force-gauging devices 102 via the communication network 124. In other implementations, a user (e.g., caregiver, medical personnel, therapist, etc.) can select devices to connect to via an I/O device 130. The force-gauging device can comprise a finger transducer device 202 and/or an orofacial transducer device 402, as described above. In some implementations, the processor 120 is configured to calibrate the force-gauging device 102.

An assessment protocol is accessed (i.e., selected, generated) for the patient based upon the one or more force-gauging devices (Block 704). Module 132 is configured to cause the processor 120 to build one or assessment protocols for the patient utilizing the connected force-gauging devices 102. For example, the processor 120 can select one or more muscle assessments for the patient that can be executed by the identified force-gauging device 102. In some implementations, a user can add one or more assessments to a protocol using the display 128 and the I/O devices 130, as described herein. For example, the user can select or input one or more assessment criteria when prompted by the display 128. Assessment criteria can comprise a variety of testing parameters including, but are not necessarily limited to: muscle groups to be tested, trial length, trial start time/end time, default criterion percentage, reaction threshold, interval time minimum/maximum, and so forth. The user can tailor the assessment protocol to the patient based on patient characteristics. The characteristics may include, but are not limited to: age, gender, weight, body type/dimensions, diagnoses, able-bodied, physical restrictions (e.g., missing limbs), and/or facial deformities. It is to be understood that the use of user input to build the assessment protocol is offered by way of example only and is not meant to be restrictive of the present disclosure. In other embodiments, the muscle assessment system 100 may apply one or more algorithms and/or machine learning techniques to generate an assessment protocol (i.e., based on patient characteristics).

The assessment protocol is executed via the one or more force-gauging devices (Block 706). The muscle assessment module 132 can cause the processor 120 to execute the assessment protocol via the connected force-gauging devices 102, as described herein. For example, the processor 120 can cause the force-gauging devices 102 to respond to a force applied by a body part of the patient (e.g., finger pressure, foot pressure, limb pressure, upper/lower lip pressure, tongue pressure, jaw pressure, lateral oral angle pressure, etc.). Data indicative of a muscle parameter is generated by the force-gauging devices (Block 708). The force-gauging devices 102 can generate an output signal corresponding to the applied force and can generate data indicative of a muscle parameter (e.g., force(s) exerted, force dynamics, strength, voluntary muscle movement, etc.). In example implementations, the force-gauging devices 102 are configured to generate data indicative of fine force regulation (i.e., a range from 0 to 100% of maximum voluntary contraction). The processor 120 can transmit the data to the computing device 104 via the communication network 124.

One or more output muscle measurements are generated (Block 710). The muscle assessment module 132 can cause the processor 120 to receive the data indicative of a muscle parameter form the force-gauging devices 102 and generate at least one output muscle measurement. For example, the processor 120 can execute one or more processes to convert the data into one or more muscle measurements. In another example, the processor 120 applies one or more data models to the data to generate one or more corresponding muscle measurements based upon the data. In some implementations, the processor 120 can utilize one or more suitable processes to generate the following output muscle measurements:

Force reaction time with simple linear regression
  Force rise time with simple linear regression
  Force slope (10-90% intercepts during recruitment/decruitment) with simple linear regression
  Force derivative (time series) for rate of force change
  Force derivative maxima during recruitment by force target by muscle tested with simple linear regression
  Force peak during recruitment by trial by force target by muscle tested with simple linear regression
  Force hold phase (mean) during two successive 1.5 second periods from 3 to 5 seconds with simple linear regression
  Force standard deviation during two successive 1.5 second periods from 3 to 5 seconds with simple linear regression
  Individual force trials display by force target and muscle tested
  Mean force (with 95% and 99% confidence intervals) time series by force target and muscle tested
  Fourier Transform (power spectrum) by force trial by force target by muscle tested
  Principal Frequency Components (f0, f1, f2) with simple linear regression
  Criterion Percentage–quantitative metric of % time patient's force within +/–target force with simple linear regression In implementations, the received data and/or the output muscle measurements may be presented via the display 128, or the like.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and microcode, and may refer to programs, routines, functions, classes, data structures, and objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A muscle assessment system, comprising:
   a force-gauging device configured to measure at least one muscle parameter, the force-gauging device including:
      at least one pressure-sensing component, the at least one pressure-sensing component configured to respond to a force applied by a subject and produce at least one output signal; and
      electrical circuitry configured to convert the at least one output signal into data indicative of at least one muscle parameter; and
   at least one computing device in communication with the force-gauging device, the at least one computing device including:
   a memory configured to store one or more modules; and
   a processor coupled to the memory, the processor configured by the one or more modules to cause the processor to:
      receive data packets indicative of the data from a receiver;
      detect connection of the force-gauging device;
      build at least one assessment protocol corresponding to the force-gauging device after detecting the connection, wherein the at least one assessment protocol is configured to assess at least one muscle parameter;
      access at least one protocol for assessing at least one muscle parameter;
      receive data packets indicative of the data associated with the at least one muscle parameter from the force-gauging device from a receiver;
      de-capsulate the data packets to obtain the data indicative of the force applied by the subject and time stamps corresponding to the force:
      associate the data indicative of the force with corresponding data within an assessment protocol based on the time stamps; and
      determine at least one muscle measurement for the subject based upon the data with respect to the at least one protocol.

2. The muscle assessment system as recited in claim 1, wherein the muscle parameter comprises at least one of muscle force exerted, force dynamics, muscle strength, and voluntary muscle control.

3. The muscle assessment system as recited in claim 1, wherein the at least one pressure-sensing component comprises a transducer.

4. The muscle assessment system as recited in claim 3, wherein the transducer includes at least one strain gauge and at least one cantilever.

5. The muscle assessment system as recited in claim 3, wherein the transducer includes at least one load cell.

6. The muscle assessment system as recited in claim 3, wherein the transducer comprises at least one of a finger transducer device and an orofacial transducer device.

7. The muscle assessment system as recited in claim 3, wherein the transducer comprises an orofacial transducer device, the orofacial transducer device comprises comprising at least one of a lip transducer, a tongue transducer, and a jaw transducer.

8. The muscle assessment system of claim 7, wherein the at least one of the lip transducer, the tongue transducer, or the jaw transducer include the electrical circuitry, the electrical circuitry configured to generate the data.

9. The muscle assessment system of claim 7, wherein the orofacial transducer device comprises the lip transducer, the tongue transducer, and the jaw transducer, wherein the lip transducer, the tongue transducer, and the jaw transducer are head-referenced so that each force generated by the lip transducer, the tongue transducer, and the jaw transducer are anatomically referenced to a facial skeleton.

10. The muscle assessment system as recited in claim 1, wherein the muscle parameter comprises a percentage of maximum voluntary contraction.

11. The muscle assessment system as recited in claim 1, wherein the at least one muscle measurement comprises at least one of force reaction time, mean force exerted, median force exerted, peak force exerted, and force hold phase.

12. A method for determining a muscle measurement based upon an exerted force, the method comprising:
    detecting a connection of a force-gauging device;
    building at least one assessment protocol corresponding to the force-gauging device after detecting the connection, wherein the at least one assessment protocol is configured to assess at least one muscle parameter;
    accessing at least one protocol based upon a force-gauging device;
    measuring, via at least one pressure-sensing component of the force-gauging device, at least one muscle parameter based upon a force applied to at least one pressure-sensing component of the force-gauging device;
    receiving data packets representing data indicative of the measured at least one muscle parameter;
    de-capsulating the data packets to obtain the data indicative of the force applied by the subject and time stamps corresponding to the force;
    associating the data indicative of the force with corresponding data within an assessment protocol based on the time stamps; and
    determining at least one muscle measurement based upon the data with respect to the at least one protocol.

13. The method as recited in claim 12, wherein the at least one pressure-sensing component comprises a transducer.

14. The method as recited in claim 13, wherein the transducer comprises an orofacial transducer device.

15. The method of claim 14, wherein the orofacial transducer device includes integrated electrical circuitry to mitigate signaling errors due to motion of a user, the integrated electrical circuitry configured to generate the data.

16. The method of claim 15, wherein the orofacial transducer device is head-referenced so that each force generated by the orofacial transducer device is anatomically referenced to a facial skeleton of the user.

\* \* \* \* \*